United States Patent
Fulton

(10) Patent No.: US 9,326,919 B2
(45) Date of Patent: May 3, 2016

(54) ENAMEL BOND FOR APPLICATION IN DENTAL PRACTICE

(71) Applicant: Laura Beth Fulton, Egg Harbor Township, NJ (US)

(72) Inventor: Laura Beth Fulton, Egg Harbor Township, NJ (US)

(*) Notice: Subject to any disclaimer, the term of this patent is extended or adjusted under 35 U.S.C. 154(b) by 148 days.

(21) Appl. No.: 14/101,577

(22) Filed: Jan. 24, 2014

(65) Prior Publication Data

US 2015/0209241 A1    Jul. 30, 2015

(51) Int. Cl.
*A61K 6/033* (2006.01)
*A61K 6/083* (2006.01)
*A61K 6/00* (2006.01)

(52) U.S. Cl.
CPC .............. *A61K 6/083* (2013.01); *A61K 6/0017* (2013.01); *A61K 6/0085* (2013.01)

(58) Field of Classification Search
CPC .................................................... A61K 6/0085
See application file for complete search history.

(56) References Cited

U.S. PATENT DOCUMENTS

| | | | |
|---|---|---|---|
| 3,679,360 A | 7/1972 | Rubin et al. | 23/109 |
| 4,080,440 A | 3/1978 | DiGiulio et al. | 424/49 |
| 4,083,955 A | 4/1978 | Grabenstetter et al. | 424/49 |
| 4,645,456 A | 2/1987 | James | 433/217.1 |
| 2010/0098761 A1* | 4/2010 | Song et al. | 424/486 |

* cited by examiner

*Primary Examiner* — Michael Pepitone
(74) *Attorney, Agent, or Firm* — Licata & Tyrrell P.C.

(57) ABSTRACT

This patent application is for Enamel Bond, a chemical solution for creating tooth enamel that successfully bonds to the dentin layer and provides both structure and composition of true, natural enamel.

4 Claims, No Drawings

ENAMEL BOND FOR APPLICATION IN DENTAL PRACTICE

BACKGROUND OF THE INVENTION

The present invention is in the technical field of oral healthcare and dental application. More particularly, the present invention is in restorative dentistry for tooth enamel loss.

There is no natural regeneration for tooth enamel and no current methods have proven successful, safe, or cost effective to re-form the enamel layer once damaged. Ameloblasts—the living cells present in the initial formation of the tooth enamel layer—are no longer present in mature enamel (Wei, Jie, Wang, Jiecheng, Shan, Wenpeng,. "Development of a Fluorapatite Cement for Dental Enamel Defects Repair", Springer Science+Business Media, Center for Biomedical Materials and Tissue Engineering, Beijing. Web). Therefore, in mature enamel there are no living cells to perform repair when the enamel layer is damaged. Dental caries (cavities) and erosion of enamel leave the dentine layer permanently exposed and subject to further caries.

From doing background research, I learned why replicating enamel's natural structure that bonds to the dentin layer has proven difficult. Tooth enamel's known composition is hydroxyapatite. The hydroxyapatite compound, $Ca_{10}(PO_4)_6(OH)_2$, can be easily synthesized in the lab but the result, as I discovered, is a chalky white paste without bonding ability (Hannig, Matthias. "Nanomaterials in Preventative Dentistry." Nature NanoTechnology Vol. 5, Aug 2010 at nature with the extension .com/naturenanotechnology of the world wide web). The resulting powder has no bonding ability. Without bonding ability, hydroxyapatite alone cannot reform the dentin enamel junction (DEJ), and cracks would penetrate tooth dentin directly.

The structure of enamel and its strong bond to the dentin layer has proven difficult to artificially replicate. Enamel is composed of hydroxyapatite (HA), the "main biomineral component of human hard tissues . . . its stoichiometry represented by the formula $Ca_{10}(PO_4)_6(OH)_2$" (Oliveira, Marise and Mansur, Herman. "Synthetic Tooth Enamel: SEM Characterization of a Fluoride Hydroxyaoatite Coating for Dentistry Applications". Mat. Res. Web. 2007).The biocompatible material of HA can be easily synthesized in the lab producing the HA paste which is a mixture of calcium hydrogen phosphate hydrate—$Ca(H_2PO_4)$—$H_2O$, and calcium hydroxide—$Ca(OH)$(Yamagishi K., Onuma K., Suzuki T., Okada F. "Materials Chemistry: A Synthetic Enamel for Rapid Tooth Repair', Nature, 433, 7028, p. 819, Science Reference Center, EBSCOhost. at <http with the extension web.ebscohost.com/scirc/detail? sid=11a81209 of the world wide web>). However, the HA material results is a chalky white powder which will not adhere to the tooth because the HA alone has no bonding ability. The HA crystal's observed in true enamel are "organized spatially into rod and interrod territories as they form" (Smith, C. E. "Cellular and Chemical Events During Enamel Maturation." Critical Reviews in Oral Biology and Medicine. 15.6 (2004): at cro with the extension-.sagepub.com/content/9/2/128 of the world wide web). The rod bond structure suggests a bonding agent is required in conjunction with HA paste to re-create enamel bond structure.

The junction between enamel and dentin, called the dentin-enamel junction (DEJ), is known for its unique "biomechanical properties that provide a crack-arrest barrier for flaws formed in the brittle enamel" (Ritchie, R., et al. "The Dentin-Enamel Junction and the Fracture of Human Teeth." Nature Materials 4.3(2005): 229. Science Reference Center. at web with the extension .ebscohost.com/sc of the world wide web). Dentin is the "main bony part of a tooth beneath the enamel, surrounding the pulp chamber and root canals" ("Dentin." American Heritage Student Science Dictionary (2009): 95. Science Reference Center. at Web. Sept. 2012. see web with the extension .ebscohost.com/etc of the world wide web). When bonding re-created enamel, it is important to consider the critical role of the DEJ region which "prevents cracks from forming in enamel, traversing the interface, and causing catastrophic tooth fractures" (Ritchie, R., et al. "The Dentin-Enamel Junction and the Fracture of Human Teeth." Nature Materials 4.3(2005): 229. Science Reference Center. at web with the extension .ebscohost.com/sc of the world wide web). The DEJ, in essence, serves like padding in a helmet; enamel is the hard, outer helmet shell and dentin the head beneath the padding. Upon impact, the padding will cushion the outer enamel shell, preventing fractures to the enamel and underneath dentin layers.

Ceramics, polymer composites, and amalgams that are currently used to refill cavity gaps cannot provide the layer of protection that only a true enamel coating is capable of doing (Hannig, Matthias. "Nanomaterials in Preventative Dentistry." Nature NanoTechnology Vol. 5, Aug 2010 at nature with the extension .com/naturenanotechnology of the world wide web). In vitro experiments have shown that the use of Hydroxyapatite "nanocrystals interact with bacterial adhesion and binding of microorganisms to tooth surface," (Smith, C. E. "Cellular and Chemical Events During Enamel Maturation." Critical Reviews in Oral Biology and Medicine. 15.6 (2004): n. page.http:// with the extension cro.sagepub.com/content/9/2/128 of the world wide web) therefore decreasing risk of enamel loss and subsequent cavities. The health significance of re-creating the enamel layer would include shielding the tooth against cavities, providing an insulation barrier for the teeth against temperature changes, protecting teeth in daily use during chewing, biting, and grinding, and decreasing risks associated with enamel loss such as gum disease—which affects eighty percent of adults—and decreasing risks correlated with more serious diseases resulting from oral complications.

Research was done to determine if there were similar patents that would provide a method description for the creation of an enamel solution for teeth and application.

U.S. Pat. No. 4,080,440, entitled Method for Reminieralizing Tooth Enamel, details a process for forming a "metastable mixture by mixing a solution containing a soluble calcium salt with a solution containing a soluble phosphate salt." This patent presents a solution that maintains the condition of natural enamel through a mouthwash but does not repair damaged enamel.

My created enamel replicates the physical and structural characteristics of natural enamel and does not 'maintain' current enamel, but would replace the enamel layer providing a natural coat. A solution of 'calcium ion and phosphate ion' alone cannot provide bonding ability to the dentin layer. However, as observed through my chemical composition with a biologically compatible bonding agent, a suitable enamel that bonds to the dentin layer is created.

U.S. Pat. No. 4,645,456 entitled Adhesive Compositions for Tooth Enamel details "a system for bonding of dental filling composites and orthodontic adhesives to tooth enamel." The process is an alternative method for highly acidic tooth etching prior to fillings.

The adhesive composites described to prepare for tooth etching are irrelevant, in the case of my invention, since teeth with enamel loss would not need etching prior to the application of my created enamel solution. The bonding agent and composition of my created enamel has been observed in the lab to have bonding ability capable to bond to surrounding enamel without etching.

U.S. Pat. No. 3,679,360 entitled Process for the Preparation of Brushite Crystals details "a process for preparation of calcium phosphate salts wherein a calcium phosphate salt is deposited from a gel medium onto the surface of a tooth . . . used to strengthen weak or damaged teeth." The surface on which apatite growth is desired must be prepared (as by roughening), and the tooth and coatings must be covered by a suitable cap for several days while the mineralization of the tooth's surface occurs.

The gel medium used to deposit the said calcium phosphate solution is applied to teeth directly, and used to "strengthen" teeth. My created enamel would not "strengthen" teeth, but when applied would repair by replacing the damaged enamel layer on teeth and provide a new, structurally identical enamel covering. The medium would be a paste rather than gel and the application time frame would be significantly less for my created enamel due to the bonding agent used (containing polymerization properties).

U.S. Pat. No. 4,083,955 entitled Process and Compositions for Reminerlzation of Dental Enamel details "a calcium and phosphate ion sequentially applied to dental enamel resulting in remineralization of subsurface dental enamel." The process explained precipitates hydroxyapatite and is combined with indium and fluoride ions creating a ZnNH4PO4. The only considerable similarity: ZnNH4PO4 created in the process patented in 4,083,955, although containing an apatite, does not result in the same formula created through my process: $Ca_{10}(PO_4)_6(OH)_{2(s)}+HEMA+H_2O_{(l)}$.

SUMMARY OF THE INVENTION

The method and the system of this invention center around the innovative concept of providing a re-created enamel with a biologically compatible bonding agent. The method of creating hydroxyapatite was based on previous studies. The addition of the bonding agent to the created hydroxyapatite—as found most suitable through lab experiments—is novel. The formulation of this invention comprises $Ca_{10}(PO_4)_6(OH)_2$, hydroxyl methacrylate (HEMA) and $H_2O$. As shown herein, this formulation forms an enamel bond useful in dental practices.

DETAILED DESCRIPTION OF THE INVENTION

The present invention provides a re-created enamel with a biologically compatible bonding agent for use in dental applications.

The composition of tooth enamel, hydroxyapatite, is known and has been created in the lab. The article "Nanomaterials in Preventative Dentistry" (Hannig, Matthias. "Nanomaterials in Preventative Dentistry." *Nature NanoTechnology* Vol. 5, Aug 2010 as nature with the extension .com/naturenanotechnology of the world wide web) provided insight to use of chemical compounds containing $Ca^{2+}$ and $HPO_4^{2-}$ to create a hydroxyapatite compound that would mimic enamel's rod-like structure. The research paper 'A Synthetic Enamel for Rapid Tooth Repair' detailed a method for creating the hydroxyapatite using a 35% $H_2O_2$ aqueous solution with an 85% solution of $H_3PO_4$ at a 4:1 ration along with 2 ml of 1.5 g fluorized-apatite powder (Yamagishi K., Onuma K., Suzuki T., Okada F. "Materials Chemistry: A Synthetic Enamel for Rapid Tooth Repair', *Nature*, 433, 7028, p. 819, Science Reference Center, EBSCOhost. Web. <http: with the extension //web.ebscohost.com/scirc/detail?sid=11a81209> of the world wide web). The simplest method for creation of the hydroxyapatite was through the mixing of $Ca(H_2PO_4)$—$H_2O$, and calcium hydroxide—$Ca(OH)$. but proportions were not specified(Yamagishi K., Onuma K., Suzuki T., Okada F. "Materials Chemistry: A Synthetic Enamel for Rapid Tooth Repair', *Nature*, 433, 7028, p. 819, Science Reference Center, EBSCOhost. at <http with the extension web.ebscohost.com/scirc/detail? sid=11a81209 of the world wide web>). This method of Yamagishi et al. of combining $Ca(H_2PO_4)$—$H_2O$, and calcium hydroxide—$Ca(OH)$, was modified herein to create the hydroxyapatite using similar, less expensive compounds and calculating ratios of how to combine compounds to yield a hydroxyapatite most similar to tooth structure.

The biologically compatible hydroxyl methacrylate (HEMA) bond was determined most suitable to bond with hydroxyapatite. Lab experiments with other bonding agents that were structurally considered biologically compatible (methacryloxyethyl trimellitate anhydride, methyl methacrylate, phenyl glycine, bi-phenyl dimethacryclate, and gluteraldehyde) did not bond in application with hydroxyapatite, whereas the HEMA bond successfully adhered to the tooth dentin layer. Since HEMA has the ability to be light cured, its addition to the hydroxyapatite also allowed a quicker (30 second through polymerization) adhesion.

Proportions of hydroxyapatite compound to added HEMA were determined based on a cure-adhesion ratio. Hydroxyapatite to HEMA equated to 4 ounces of hydroxyapatite powder: 0.15 ml HEMA liquid. The small amount of HEMA relative to the hydroxyapatite was reflected through chemical characterization of the mixed solution using X-ray diffraction which identified the created enamel composition identical to that of natural enamel The result as indicated through the x-ray diffraction test demonstrated a layer of hydroxyapatite was bonded to the dentin.

The created enamel, referred to as 'Enamel Bond' was tested to determine its likeness to natural enamel. Dental tests commonly used to test composite and filling materials were used to determine durability, strength, and bond to the dentin layer. Microleakage tests revealed Enamel Bond's durability equivalent to natural enamel; Vickers Hardness concluded Enamel Bond's structure and dentin bond to rival true, natural enamel; and SEM analysis revealed rod-bonded structures identical to natural enamel.

Accordingly the Enamel Bond of the present invention is expected to improve oral health by shielding teeth against cavities, providing an insulation barrier for teeth against temperature changes, protecting teeth in daily use during, for example, but not limited to, chewing, biting and grinding, decreasing risks associated with enamel loss such as gum disease, which affects eighty percent of adults, and other more serious diseases resulting from oral complications, providing patients with less sensitivity and pain from exposed dentin, and providing patients with whiter and better shaped teeth.

Advantages of the Enamel Bond of the present invention include adherence when photoionized in a minimal time frame, providing a protective shield against bacteria and a demonstrated resistance to microleakage.

Enamel Bond in application also has safety advantages as compared to amalgam and resin-based fillings. For example, Enamel Bond does not contain toxic metals or endocrine disrupting plastics. Amalgam fillings are not safe substitutes for natural enamel; many contain lead and mercury which leach out of the fillings over time. Resin-based composite fillings, though containing no mercury or lead, have been known to contain BPA. an endocrine disruptor which is released from the fillings into the mouth in the first ten hours after application. Enamel Bond is also compatible to temperature change. Amalgam fillings are sensitive to heat and cold, offering discomfort. In addition, Enamel Bond shows high durability and is resistant to microleakage; the repair/replacement of amalgam fillings is frequent due to high microleakage.

The Enamel Bond solution of the present invention is applicable in re-enameling. With the use of the Enamel Bond solution, a new enamel layer can be applied to repair teeth damaged due to demineralization of dental enamel attributed to attrition (tooth clenching), abrasion (hard brushing), abfraction (stress fractures), and corrosion (acidic context). The Enamel Bond solution can also be used to provide a new enamel layer for people who have lost enamel due to acid reflux, consumption of acidic foods, bulimia, binge drinking, medically compromised immune systems, antibiotics used prior to adult teeth development, traumatic injury, teeth grinding, and wear over time.

The following examples further illustrate the present invention.

EXAMPLES

Example 1

Processes for Preparation of the Enamel Bond Solution—Combination of Calcium Hydroxide ($Ca(OH)_2$) and Calcium Phosphate ($Ca(H_2PO_4)_2$) with a HEMA Bond for Adherence (and Polymerization)

The Enamel Bond formula $Ca_{10}(PO_4)_6(OH)_2$ is prepared through the suspension of the chemical solutions of calcium hydroxide and calcium phosphate. A suspension with a concentration of 0.30 M $Ca(OH)_2$ is prepared by measuring 22.23 grams (approx. +−0.1 grams) of the base using an analytical balance. Distilled water is added to the bottom of a 1 liter volumetric flask before the $Ca(OH)_2$ could be added since a compound should be added to water. The measured grams of $Ca(OH)_2$ is added to the distilled water in the volumetric flask and distilled water is added to the flask until the fill line (indicating 1L) is reached. The solution of 0.3M $Ca(OH)_2$ in the volumetric flask is then mixed under vigorous stirring (using magnetized stirring rods or by manual stirring) for 15 minutes at room temperature. A suspension with a concentration of 0.12 M aqueous solution of $Ca(H_2PO_4)_2.H_2O$ is prepared by measuring 30.25 grams (approx. +−0.1 grams) of the acid using an analytical balance. Distilled water is added to the bottom of a second, clean 1 liter volumetric flask before the $Ca(H_2PO_4)_2.H_2O$ could be added. The measured grams of $Ca(H_2PO_4)_2.H_2O$ is added to the distilled water in the volumetric flask, and distilled water is added to the flask until the fill line (indicating 1L) is reached. The $Ca(H_2PO_4)_2.H_2O$ suspension, like the $Ca(OH)_2$ suspension, is mixed using magnetized stirring rods for 15 minutes at room temperature. Once both the $Ca(H_2PO_4)_2.H_2O$ and $Ca(OH)_2$ suspensions have been prepared, they are combined. The $Ca(H_2PO_4)_2.H_2O$ is added to the $Ca(OH)_2$ and the resulting suspension is stirred for one hour at room temperature (using stirring rods and a magnetized bottom plate). The stirring rods are removed after one hour and resulting suspension is then aged for 12 hours at room temperature.

After the suspension has remained untouched for 12 hours, the supernacent (water above the compound) is decanted and the precipitate is subjected to vacuum filtering. A Büchner funnel is prepared for the decanting by aligning the filter base with filter paper, attaching a rubber suction tube to a source of running water, and placing a Florence flask beneath the funnel to collect water from the solution decanted. The suspension is vacuum filtered by pouring the suspension into the Büchner funnel's top while a source of running water is connected to the funnel, causing pressure and suctioning in the tube. The paste remaining on the filter paper remaining after funneling is then dried using an oven set at 110° C. for 24 hours.

The resulting enamel powder produced after heating is $Ca_{10}(PO_4)_6(OH)_{2(s)}$ (by composition-hydroxyapatite). The hydroxyapatite is introduced to a biologically compatible HEMA bond in solution which chemically combines to produce an "Enamel Bond" (enamel composition with bonding ability). The HEMA bond is introduced to the hydroxyapatite in the form of liquid droplets. Using a volumetric pipette, the HEMA bond is combined with the hydroxyapatite in a ratio of 0.15 mL HEMA bond per 4 ounces of hydroxyapatite powder. The resultant paste can be directly applied as Enamel Bond on teeth or can be stored until time of application.

The balanced equation for the enamel is shown below:

Enamel

With Bonding

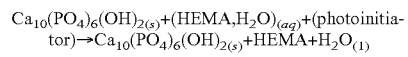

Example 2

Data Collection and Analysis

X-ray diffraction was used to identify the chemical components of hydroxyapatite and Enamel Bond. Enamel Bond is HA with the addition of the HEMA bond.

Microleakage cycling after a simulated three years in the mouth revealed that the Enamel Bond is equivalent in durability to natural enamel. From Microleakage results, it is expected that the Enamel Bond durability, since it is similar to the natural enamel, will last a lifetime if properly taken care of.

Vickers Hardness tests of Enamel Bond tablets showed that, compared to natural enamel alone, there is no significant difference between the hardnesses. The Enamel Bond had an average hardness index of 3.83 HV which provides just as hard a surface as the natural enamel which ranges from 2.9-3.9 HV. Statistical analysis of the Vickers Hardness for natural enamel and the created enamel demonstrated that there was no significant difference in hardness.

SEM analysis showed that the structure of Enamel Bond is a replication to natural enamel as indicated by the observed rod-like bond structures.

Additional Sources

"Calcium and Tooth Decay." *Science News For Kids* (2007): 3. *Science Reference Center*. Web. Minnesota Reports Available. <http:web.ebscohost.com/etc.

Chatzistavrou, Xanthippi. "Innovative Approaches to Regenerate Enamel and Dentin" *International Journal of Dentistry*, vol. 2012, Article ID 856470, 5 pages, 2012.

"Enamel". *American Heritage Student Science Dictionary* (2009);115. *Science Reference Center*. Web. <http://web.ebscohost.com/scirc/detail?sid=9a861d1>

Goho, Alexandra. "Something to Chew On Hard facts about tooth enamel." *Science News*. 167.20 (2005): 312. Web. <http://www.phschool.com/science/science_news Hashemeyer, Brian. "Chelates, Complexes & Salts of Multivalent Cations in Aqueous Solutions." BRANDT. Critical Stability Constants http://www.fluidfertilizer.com/Forum Reis, S. "Durability of Enamel Bonding Using One-step Self-etch Systems on Ground and Unground Enamel". *Operative Dentistry*: March 2009, Vol. 34, No. 2, pp. 181-191.

Rijck, G., and E. Schrevens. "Catonic Specification In Nutrient Solutions As a Function of pH." *Faculty of Agricultural and Applied Biological Sciences*. 42. (2008): n. page. Web.

Tanaka, R, Y Shibata, M Atsufumi, and M Takashi. "Mineralization Potential of Polarized Dental Enamel." *PLoS ONE*. 4.6 (2009): n. page.

Yin, Yujing. "Chemical Regeneration of Human Tooth Enamel Under Near-Physiological Conditions." *RSC Publishing*. (2011): n. page. Web. <http://pubs.rsc.org/en/content/articlelanding/2009/cc/b911407f>.

What is claimed is:

1. A composition consisting of:
    (a) $Ca_{10}(PO_4)_6(OH)_2$
    (b) hydroxyl methacrylate (HEMA) and
    (c) $H_2O$.

2. The composition of claim 1 wherein the $Ca_{10}(PO_4)_6(OH)_2$, HEMA and $H_2O$ are in a ratio of 3:7:1, respectively.

3. A method for restoring enamel on a tooth of a subject in need, said method comprising applying to the tooth the composition of claim 1.

4. A method for restoring enamel on a tooth of a subject in need, said method comprising applying to the tooth the composition of claim 2.

* * * * *